United States Patent [19]

Stucky et al.

[11] Patent Number: 5,294,710

[45] Date of Patent: Mar. 15, 1994

[54] N-5-PROTECTED 2,5-DIAMINO-4,6-DICHLOROPYRIMIDINES AND PROCESS FOR THEIR PRODUCTION

[75] Inventors: Gerhard Stucky; Felix Previdoli, both of Brig-Glis, Switzerland

[73] Assignee: Lonza Ltd., Gampel/Valais, Switzerland

[21] Appl. No.: 6,525

[22] Filed: Jan. 21, 1993

[30] Foreign Application Priority Data

Jan. 22, 1992 [CH] Switzerland .................. 179/92

[51] Int. Cl.$^5$ ............... C07D 239/42; C07D 239/52; C07D 239/30
[52] U.S. Cl. ................................. 544/320; 544/332
[58] Field of Search ................. 544/332, 320

[56] References Cited

FOREIGN PATENT DOCUMENTS 2116554 9/1983 United Kingdom .
WO9101310 2/1991 World Int. Prop. O. .

OTHER PUBLICATIONS

Legraverend et al., Synthesis, (1990), pp. 587 to 599.
Greene, Theodora W., "Protective Groups In Organic Synthesis", John Wiley & Sons (1981).

Primary Examiner—John M. Ford
Attorney, Agent, or Firm—Fisher, Christen & Sabol

[57] ABSTRACT

N-5-protected 2,5-diamino-4,6-dichloropyrimidines of general formula:

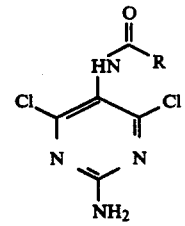

wherein R is an alkoxy group or a trifluorometyl group, are valuable intermediate products for the production of pharmaceutical agents with antiviral properties. The above-mentioned compounds are produced by cyclization of an N protected amino malonic acid ester with guanidine in the presence of an alkali alcoholate and then chlorination of the resulting N-5-protected 4,6-dihydroxy-2,5-diaminopyrimidine.

6 Claims, No Drawings

N-5-PROTECTED 2,5-DIAMINO-4,6-DICHLOROPYRIMIDINES AND PROCESS FOR THEIR PRODUCTION

BACKGROUND OF THE INVENTION

1. Field Of The Invention

The invention relates to N-5-protected 2,5-diamino-4,6-dichloropyrimidines of the general formula:

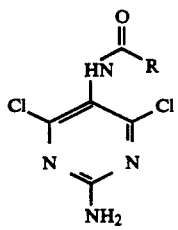

wherein R is an alkoxy group or a trifluoromethyl group, as well as a process for their production. These compounds form valuable intermediate products for the production of antiviral nucleotide derivatives—see PCT Published Application WO 91/01310.

2. Background Art

Various syntheses for the production of 2,5-diamino-4,6-dichloropyrimidines are known. Thus, Legraverend et al. in "Synthesis", (1990), pages 587 to 589, reports that an amino malonic acid ethyl ester can be cyclized with guanidine in the presence of sodium alcoholate to 4,6-dihydroxy-2,5-diaminopyrimidine with a yield of 64 percent. The dihydroxypyrimidine is then reacted to the desired dichloropyrimidine with phosphorus oxychloride/phosphorus(V)-chloride in the presence of a quaternary ammonium salt under drastic reaction conditions with a yield of 32 percent.

Legraverend et al. indicates that the chlorination with phosphorus oxychloride takes place unsuccessfully. But the necessity of additional reagents such as phosphorus(V)chloride, of quaternary ammonium salts or of drastic reaction conditions and the thus achievable modest yields, is an obvious drawback of this synthesis. A sudden improvement of the synthesis was disclosed in PCT Application W091/01310. The chlorination step of 4,6-dihydoxy-2,5-diaminopyridine to the desired 4,6-dichloro derivative is performed in PCT Application W091/01310 with phosphorus oxychloride alone as the chlorination agent in the presence of a quaternary ammonium chloride or a hydrochloride of a tertiary amine. The yields were able to be increased to 50 to 60 percent. But the use of substantial amounts of ammonium salts or amino salts, that result as salt load and have to be fed to a waste disposal still constitute a considerable drawback.

BROAD DESCRIPTION OF THE INVENTION

The main object of the invention is to provide a synthesis method that does not exhibit the above-mentioned drawbacks. Other objects and advantages of the invention are set out herein or are obvious herefrom to one skilled in the art.

The objects and advantages of the invention are achieved by the N-5-protected 2,5-diamino-4,6-dichloropyrimidine derivatives of the invention and the production process of the invention.

The invention involves N-5-protected 2,5-diamino-4,6-dichloropyrimidines of the formula:

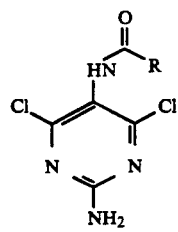

wherein R is an alkoxy group or a trifluoromethyl group.

The invention also involves a process for the production of the N-5-protected 2,5-diamino-4,6-dichloropyrimidines of the formula I. The process includes cyclizing an N-protected amino malonic acid ester of the formula:

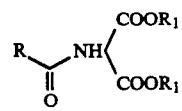

wherein $R_1$ is a $C_1$–$C_4$ lower alkyl group and R has the above-mentioned meaning, with guanidine in the presence of an alkali alcoholate to an N-5-protected-4,6-dihydroxy-2,5-diaminopyrimidine of the formula:

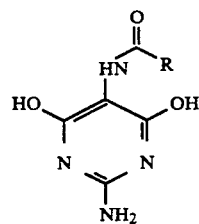

wherein R has the above-mentioned meaning. The pyrimidine of formula III is then reacted with phosphorus oxychloride to provide the end product.

The N-5-protected 2,5-diamino-4,6-dichloropyrimidines of formula I are intermediate products for the production of antiviral nucleotide derivatives - see PCT Published Application W091/01310 (published on Feb. 7, 1991), and Legraverend et al., ibid..

The invention further includes N-5-protected 2,5-diamino-4,6-dihydroxypyrimidines of the formula:

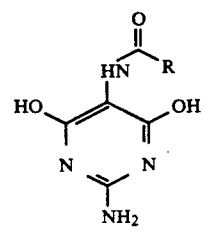

wherein R is an alkoxy group or a trifluoromethyl group, which are intermediate products in the invention process for preparing the invention products.

DETAILED DESCRIPTION OF THE INVENTION

The N-5-protected 2,5-diamino-4,6-dichloropyrimidines according to the invention are compounds that have not been previously described in the prior art. Preferred representatives of these compounds of general formula I are N-5-($C_1$–$C_4$)alkoxycarbonyl-2,5-diamino-4,6-dichloropyrimidines (R=$C_1$–$C_4$ alkyl).

According to the invention, in the first process step, an N-protected amino malonic acid ester of the formula:

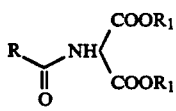

wherein $R_1$ is a $C_1$–$C_4$ lower alkyl group and R has the above-mentioned meaning, is cyclized with guanidine in the presence of an alkali alcoholate to N-5-protected-4,6-dihydroxy-2,5-diaminopyrimidine of the formula:

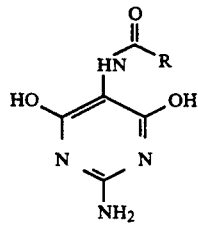

in which R has the above-mentioned meaning. The intermediate compounds of formula III have not been previously described in the prior art and, therefore, are also part of the invention.

The N-protected amino malonic acid esters of the formula II used as the initial products (or starting materials) can be produced in a simple way from an amino malonic acid ester, in the case where R is an alkoxy group, by reaction with a corresponding haloformic acid alkyl ester, or in the case where R is a trifluoromethyl group, by reaction with a trifluoroacetyl halide.

The alkali alcoholate is suitably produced in situ from the respective alkali metal and the respective alcohol. Usually the alcohol is used in excess, and the excess alcohol is simultaneously used as the solvent.

Preferably the cyclization reaction is performed in the presence of in situ formed sodium methylate in methanol or sodium ethylate in ethanol. Suitably the cyclization reaction takes place at a temperature between room temperature and 80° C., preferably under reflux conditions.

The isolation of the N-5-protected 4,6-dihydroxy-2,5-diaminopyrimidine of general formula III can take place in a way known to one skilled in the art.

Subsequently the N-5-protected 4,6-dihydroxy-2,5-diaminopyrimidine according to the invention is chlorinated with phosphorus oxychloride to the desired end product of general formula I. The chlorination with phosphorus oxychloride surprisingly takes place without additives at a temperature of suitably 80° C. to the reflux temperature of the phosphorus oxychloride, preferably at 80° C. to 90° C. The phosphorus oxychloride, used here in excess, acts additionally as the solvent. Although an additional inert solvent can be added, it provides no advantages. The chlorination, as a rule, is completed after 6 hours maximum.

After working up in a way usual to one skilled in the art, the N-5-protected 4,6-dichloro-2,5-diaminopyrimidine can be isolated in good yield and purity.

EXAMPLE 1

(a) N-butyloxycarbonyl-amino malonic acid diethyl ester (R=OBu)

To an ice-cold suspension of 15 g (70.87 mmol) of amino malonic acid ethyl ester hydrochloride in 180 ml of methylene chloride, 10.8 g (75 mmol) of chloroformic acid butyl ester and then 14.7 g (145 mmol) of triethylamine were added within several minutes. In this case the temperature was constantly maintained under 20° C. After the addition was completed, the reaction was stirred for another 75 minutes at room temperature. The reaction solution was diluted with 80 ml of $CH_2Cl_2$, washed with two portions of water, and dried on $Na_2SO_4$. After concentration by evaporation on a rotary evaporator, 18.8 g (96 percent) of pure title product was obtained. Other data concerning the product was:

$^1$H-NMR ($CDCl_3$, 300 MHz) δ in ppm: 0.92 (t, 3H); 1.31 (t, 6H); 1.3–1.45 (m, 2H); 1.55–1.65 (m, 2H); 4.1 (t, 2H); 4.2–4.4 (m, 4H); 5.0 (d, 1H); 5.1 (d, 1H); 5.7 (d, 1H); 5.95 (d, 1H).

(b) 5-(N-butyloxycarbonyl-2-amino-4,6-dihydroxypyrimidine (R=OBu)

To a solution of 4.2 g (180 mmol) of sodium in 130 ml of ethanol, 11 g (115 mmol) of guanidine hydrochloride was added. After 10 minutes the suspension was mixed with 18 g [65 mmol of the product from step (a)] and refluxed. After one hour the reaction solution was cooled to 40° C., adjusted with conc. HCl to pH 2, and the ethanol was distilled off for the most part on a rotary evaporator. The evaporation residue was suspended in 100 ml of $H_2O$, cooled in an ice bath and then the product filtered off. After washing with three portions of cold water and drying in a vacuum drying oven at 100° C., 13.45 g (85 percent) of the title product was obtained. Other data concerning the product was:

$^1$H-NMR (DMSO, 300 MHz) δ in ppm: 0.9 (t, 3H); 1.1–1.6 (m, 4H); 3.85–3.95 (m, 2H); 6.22 (2s, 2H); 7.0 (2s, 2H); 7.08 (2s, 1H); 7.3 (2s, 1H); 10.0–11.0 (br, 2H).

(c) 5-(N-butyloxycarbonyl)-2-amino-4,6-dichloropyrimidine R=OBu)

A suspension of 3 g (12.39 mmol) of the product from step b) in 25 ml of phosphorus oxychloride was heated for 2 hours to 90° C. In this way the solid dissolved slowly. The excess $POCl_3$ was concentrated by evaporation on a rotary evaporator, and the residue poured onto ice. At the same time the temperature rose to 50° C. At this temperature it was adjusted to pH 3 and stirred for another hour. The suspension was cooled to 5° C. and the product filtered. After drying in a vacuum drying oven at 40° C., 2 g (57 percent) of the title product with a content of 96 percent (according to GC/Fl %) was obtained. The melting point of the product was 161° to 164° C. Other data concerning the product was:

$^1$H-NMR (CDCl$_3$, 300 MHz) δ in ppm: 0.8–1.1 (m, 3H);
1.2–1.9 (m, 4H);
4.1–4.3 (m, 2H);
5.4 (s, 2H);
5.9–6.2 (m, 1H).

Anal.cld. for CH$_9$H$_{12}$Cl$_2$N$_2$O$_2$ (279): C=37.99 H=4.3 N=20.0
Fnd.: C=37.7 H=4.4 N=19.6

EXAMPLE 2

(a) 5-(N-methoxycarbonyl)-2-amino-4,6-dihydroxypyrimidine (R=OMe)

60 g of a 30 percent sodium methanolate solution in methanol was instilled within 5 minutes in a suspension of 30 g (0.128 mol) of N-methoxycarbonyl-aminomalonic acid diethyl ester and 22 g (0.23 mol) of guanidine hydrochloride in 300 ml of methanol. Then the suspension was refluxed for 160 minutes. The methanol was concentrated by evaporation on a rotary evaporator, the residue taken up in 150 ml of H$_2$O, the pH adjusted to 3 to 4 and, after cooling to 5° C., the product was filtered off, washed three times with 30 ml of H$_2$O each and dried on high vacuum at 100° C. 17.3 (67 percent) of the title product was obtained. Other data concerning the product was:

$^1$H-NMR (DMSO, 300 MHz) δ in ppm: 3.55 (s, 3H);
6.7 (s, 2H);
7.2 (s, 1H);
7.45 (s, 1H);
10.0–11.0 (br, 2H).

(b) 5-(N-methoxycarbonyl)-2-amino-4,6-dichloropyrimidine (R=OMe)

A suspension of 3 g (15 mmol) of the product of step (a) in 35 ml of POCl$_3$ was heated to 88° C. In the course of this the solid dissolved slowly. After 5.5 hours the excess phosphorus oxychloride was distilled off on a rotary evaporator and the very viscous residue was poured onto ice. At the same time the temperature rose to 50° C. It was stirred for another 1.5 hours. After cooling to 5° C. the solid was filtered off. 1.66 g (47 percent) of the title product with a content of 97 percent (GC) was obtained. The filtrate was extracted three times with ethyl acetate, the common organic phase dried on Na$_2$SO$_4$ and concentrated by evaporation on a rotary evaporator. Another 0.65 g (18 percent) of the title product with a content of 87 percent (according to GC) was obtained. Other data concerning the product was:

$^1$H-NMR (DMSO, 300 MHz) δ in ppm: 3.7 (s, 3H);
7.62 (s, 2H);
8.8 (s, 1H);
9.1 (s, 1H).

EXAMPLE 3

(a) 5-(N-trifluoroacetyl)-2-amino-4.6-dihydroxypyrimidine (R=CF$_3$)

To a 50° C. solution of 5.3 g (0.23 mol) of sodium in 600 ml of ethanol, 11.4 g (0.12 mol) of guanidine hydrochloride was added and allowed to stir for 10 minutes. 29.75 g (0.11 mol) of N-trifluoroacetylamino malonic acid diethyl ester was added to the white suspension within 30 minutes. The viscous suspension was heated to 80° C. and allowed to react for 4 hours. Then another 4 g (40 mmol) of guanidine hydrochloride was added and refluxed for another hour. The reaction mixture was cooled to room temperature, filtered and the filter cake was rewashed with some ethanol. The solid was taken up in 350 ml of water and the ph was adjusted to approximately 5 with conc. HCl. The suspension was cooled in an ice bath, filtered and the product dried in a vacuum at 40° C. 16.4 g (62 percent) of violet solid was obtained. Other data concerning the product was:

$^1$H-NMR DMSO 6.9 (br, s, 2H);
9.7 (s, 1H);
10.2–11.2 (br, 2H).

(b) 5-(N-trifluoroacetyl)-2-amino-4,6-dichloropyrimidine (R=CF$_3$)

A suspension of 15 g (63 mmol) of the product from step a) in 100 ml of POCl$_3$ was refluxed for 2 hours. In this way the solid dissolved gradually. Then the reaction mixture was cooled to room temperature, the excess phosphorus oxychloride distilled off and the viscous residue poured onto ice. In this way the temperature rose to 40° C. The pH was adjusted to approximately 4 and after an hour at this temperature the product was isolated by extraction with four portions of ethyl acetate. The common organic phases were dried on Na$_2$SO$_4$ and concentrated by evaporation on a rotary evaporator. 5.97 g (35 percent) of the title product was obtained. Other data concerning the product was:

$^1$H-NMR DMSO 7.85 (s, 2H);
11.4 (s, 1H).

What is claimed is:

1. A N-5-protected 2,5-diamino-4,6-dichloropyrimidine of formula:

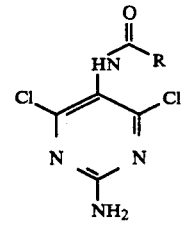

wherein R is a C$_1$–C$_4$-alkoxy group or a trifluoromethyl group.

2. A process for the production of a N-5-protected 2,5-diamino-4,6-dichloropyrimidine of formula:

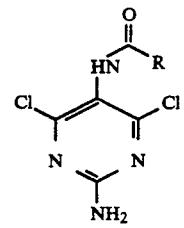

wherein R$_1$ is a C$_1$–C$_4$ lower alkyl group and R is a C$_1$–C$_4$-alkoxy group or a trifluoromethyl group, comprising cyclizing an N-protected amino malonic acid ester of formula:

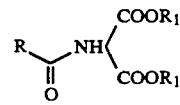

wherein R$_1$ has the above-mentioned meaning and R has the above-mentioned meaning, with guanidine in the presence of an alkali alcoholate to a N-5-protected-4,6-dihydroxy-2,5-diaminopyrimidine of formula:

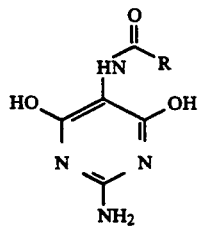

III wherein R has the above-mentioned meaning, and reacting the pyrimidine of formula III with phosphorus oxychloride to provide the end product.

3. The process according to claim 2 wherein the cyclization of the N-protected amino malonic acid ester takes place in the presence of sodium methanolate in methanol or sodium ethanolate in ethanol at a temperature between room temperature and the boiling point of the respective alcohol.

4. The process according to claim 3 wherein the chlorination takes place at a temperature between 80° C. and the boiling temperature of phosphorus oxychloride.

5. The process according to claim 2 wherein the chlorination takes place at a temperature between 80° C. and the boiling temperature of phosphorus oxychloride.

6. A N-5-protected 2,5-diamino-4,6-dihydroxypyrimidine of formula:

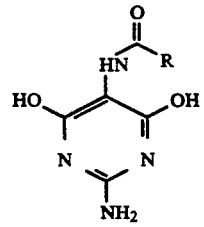

III wherein R is a $C_1$–$C_4$-alkoxy group or a trifluoromethyl group.

* * * * *